United States Patent [19]

Fox, Jr.

[11] 3,993,750

[45] Nov. 23, 1976

[54] AQUEOUS HYPERTONIC SOLUTION AND COMPOSITIONS USEFUL FOR PREPARATION OF SAME

[75] Inventor: Charles L. Fox, Jr., New York, N.Y.

[73] Assignee: Research Corporation, New York, N.Y.

[22] Filed: Dec. 20, 1974

[21] Appl. No.: 534,883

[52] U.S. Cl. .............................. 424/128; 424/153; 424/154; 424/156; 424/180
[51] Int. Cl.² ................. A61K 31/70; A61K 33/06; A61K 33/10; A61K 33/14
[58] Field of Search ........... 424/128, 153, 154, 156, 424/180

[56] References Cited
UNITED STATES PATENTS
3,676,553 7/1972 Reynolds ............................ 424/153

OTHER PUBLICATIONS
The Pharmaceutical Journal, p. 418, Dec. 1952, vol. 169.

P.D.R. Quarterly Supplement, No. 3 July 1966 p. 31.

*Primary Examiner*—Stanley J. Friedman
*Attorney, Agent, or Firm*—Cooper, Dunham, Clark, Griffin & Moran

[57] ABSTRACT

An aqueous hypertonic solution useful in the treatment of a human suffering from a burn injury and the like comprises on the basis of one liter of solution about 200–300 mEq sodium, about 145-215 mEq chloride, about 55–85 mEq bicarbonate or acetate or lactate, the mEq sodium to chloride ratio being 1.4. An example of the above hypertonic solution is an aqueous solution containing per liter 225 mEq sodium, 160 mEq chloride, 73 mEq acetate, about 5 mEq potassium and about 3 mEq magnesium, the solution having a pH of about 8.3, preferably having a pH of about 6.0 upon pH adjustment by the addition of hydrochloric acid.

14 Claims, No Drawings

AQUEOUS HYPERTONIC SOLUTION AND COMPOSITIONS USEFUL FOR PREPARATION OF SAME

The invention described herein was made in the course of work under a grant or award from the Department of Health, Education, and Welfare.

This invention relates to solutions, and compositions for the preparation of the same, useful in the treatment of persons suffering from shock or injury, such as a burn. Various solutions, hypotonic, isotonic and hypertonic, have been suggested in the treatment of persons suffering from trauma, such as burn shock. For the most part, however, such sections have not been completely satisfactory when administered to the patient intravenously or orally. Examples of such solutions and the preparation thereof are described in U.S. Pat. Nos. 3,676,553 and 3,821,368 and are described in the paper entitled "Comparative Efficacy of Hypo-, Iso- and Hypertonic Sodium Solutions in Experimental Burn Shock", which I have co-authored with John W. Stanford, published in SURGERY, Vol. 75, No. 1, pp. 71–79, January 1974, and on the references cited therein, which paper also discloses comparative data setting forth the efficacy of the hypertonic solutions in accordance with my invention as compared with other hypotonic, isotonic and hypertonic solutions. Of interest also in connection with this invention is the publication entitled "Fluid and Electrolytes", published 1970 by Abbott Laboratories, North Chicago, Illinois. The disclosures of the above-identified patents, the above-identified Abbott Laboratories publication and my above-identified paper and the references cited therein are herein incorporated and made part of this disclosure.

It is an object of this invention to provide improved solutions useful for administration, such as by intravenous injection, to patients suffering from burn injuries and the like.

It is another object of this invention to provide an improved hypertonic solution, and compositions useful in the preparation thereof, suitable for administration to patients suffering from an injury, such as a burn injury or shock.

How these and other objects of this invention are achieved will become apparent in the light of the foregoing disclosure. In at least one embodiment of the practices of this invention, at least one of the foregoing objects will be achieved.

In accordance with this invention, it has been discovered that an aqueous solution comprising on the basis of 1 liter of solution about 200–300 mEq sodium, about 145–215 mEq chloride, about 55–85 mEq bicarbonate or acetate or lactate, the mEq sodium to chloride ratio therein being about 1.4, is particularly useful as a hypertonic solution for administration to a patient suffering from trauma or shock, such as a burn injury. Desirably, a hypertonic solution in accordance with this invention, in addition to having the above-indicated composition, also includes in its make-up about 1.5–2.5 mEq magnesium, about 3.5–5.5 mEq potassium and up to about 5.5 mEq calcium, such as about 3–5.5 mEq calcium. Also, desirably, solutions in accordance with this invention might include about 2.5–3.5 mEq phosphates and, if desired, up to about 5% by weight dextrose. The hypertonic solutions in accordance with this invention tend to be alkaline, a pH of above 7, e.g. a pH of about 8.3. Desirably, particularly when calcium is present in the hypertonic solution, the pH of the solution is adjusted to be acidic, i.e. a pH below 7.0, e.g. about 6.0, by the addition of an acid, such as hydrochloric acid. Also, if desired, there may be included in the aqueous solution in accordance with this invention phosphates up to about 3.8 mEq, such as about 2.5–3.5 mEq, and additionally, if desired, up to about 5% by weight dextrose based on said solution.

Exemplary of the hypertonic solutions in accordance with this invention would be a solution containing per liter about 235 mEq Na, about 160 mEq chloride, about 75 mEq bicarbonate or acetate or lactate, about 2 mEq magnesium, about 5 mEq potassium and about 3 mEq calcium, which solution would initially, i.e. when formed, have a pH of about 8.3. The solution is desirably adjusted for stability purposes, e.g. to prevent precipitation of calcium, by the addition of hydrochloric acid to a pH of about 6.0. If desired, the solution could contain a minor amount of dextrose, up to about 8%, e.g. 5%, by weight, more or less, and also, if desired, there may be included in the solution up to about 2.5–3.5 mEq phosphates.

Also exemplary of a hypertonic solution in accordance with this invention would be a solution containing per liter about 225 mEq sodium, about 160 mEq chloride, about 73 mEq bicarbonate as acetate or, if desired, as lactate, and containing about 5 mEq potassium and about 3 mEq magnesium. For stability purposes, it is usually desirable to prepare the solutions in accordance with this invention with lactate or acetate rather than bicarbonate since bicarbonate would be obtained by metabolism of the lactate or acetate upon administration of the solution.

In the solutions of this invention, the sodium to chloride ratio would be substantially at about 1.4, the ratio of sodium to chloride in normal plasma. In normal plasma, the amount of sodium present per liter is about 140 mEq, chloride is about 103 mEq, bicarbonate about 27 mEq, potassium about 5 mEq, calcium about 5 mEq and magnesium about 3 mEq.

The preparation of the hypertonic solutions in accordance with this invention is readily carried out by the addition of water-soluble salts which yield the cations and anions making up the hypertonic solutions and in the necessary amounts. Suitable water-soluble salts which are useful in the preparation of hypertonic solutions in accordance with this invention include NaCl, KCl, $NaHCO_3$, $KHCO_3$, $Na_2SO_4$, $MgCl_2$, Na acetate, K acetate, Na lactate, K lactate, $MgSO_4$, $Na_2HPO_4$, $K_2HPO_4$. Any desired or necessary adjustment of pH can be obtained by the addition of suitable acids or bases, such as HCl, $H_2CO_3$, NaOH, KOH and $CO_2$.

As indicated hereinabove, the solid compositions containing the requisite water-soluble salts in suitable proportions can be formed, e.g. as simple admixture thereof, such that when the admixture is added to a sufficient amount of water there would be produced a hypertonic solution having the composition in accordand with this invention. Such solutions could be administered orally to the patient.

Hypertonic solutions in accordance with this invention have been administered to humans in post-operative therapy and suffering from burns. It has been observed that, particularly in connection with the administration, e.g. intravenous administration, of the hypertonic solutions in accordance with this invention, less solution volume need be administered and less edema or swelling, particularly in the area of the burn, is observed, thereby tending to avoid surgical procedures to reduce undue or dangerous swelling. Further, upon the administration of hypertonic solutions in accordance with this invention, good urine volumes were received.

The dosages of the hypertonic solutions in accordance with this invention are usually about ⅔ to ½ that of isotonic solutions, usually 150 ml per kilogram of body weight or with respect to burn patients about 2–3 ml per one percent body burn surface per kilogram body weight.

Set forth in accompanying Table I are the compositions of various resuscitation solutions, isotonic and hypertonic, including the composition of hypertonic solution in accordance with this invention and the composition of normal plasma.

ing in the hypertonic solution of this invention, solution J, the correct Na:Cl ratio. Accordingly, the hypertonic solutions of this invention provide the advantages of resuscitation without excess water, chloride or bicarbonate. Actually, the degree of hypertonicity approximates that lost after trauma and thus an excess of sodium is also avoided.

Previous workers have demonstrated the superiority of hypertonic solutions, resuscitation with the use of smaller volumes and less edema and gain of weight. However, hypertonic solutions, such as solution J, in accordance with this invention and possessing the advantages thereof have not heretofore been available. Experimental studies carried out employing the hypertonic solutions in accordance with this invention show greater safety and superiority in terms of greater sur-

TABLE I

| | A | B | C | D | E | F | G | H | I | J |
|---|---|---|---|---|---|---|---|---|---|---|
| COMPARISON OF RESUSCITATION SOLUTIONS, mEq/l. | | | | | | | | | | |
| | | | ISOTONIC SOLUTIONS | | | | HYPERTONIC SOLUTIONS | | | |
| | Normal Plasma | 0.9% NaCl | Ringer (1880) | Lactate-Ringers (Hartmann-1932) | m/6 Na Lactate | Darrow (1945) | Normosol*** (Balanced Electrolyte) (Fox 1952) | 3% NaCl | Monafo (1970) | Monafo (1973) | Fox (1974) |
| Na | 140 | 154 | 147 | 130 | 167 | 122 | 140 | 570 | 300 | 250 | 225 |
| Cl | 103 | 154 | 157 | 109 | 0 | 104 | 98 | 570 | 100 | 150 | 160 |
| Na/Cl | 1.4 | 1.0 | 0.9 | 1.2 | — | 1.2 | 1.4 | 1.0 | 3.0 | 1.7 | 1.4 |
| $HCO_3$ | 27 | 0 | 0 | 28* | 167 | 53* | 50** | 0 | 200* | 100* | 73** |
| K | 5 | 0 | 4 | 4 | 0 | 35 | 5 | 0 | 0 | 0 | 5 |
| Ca | 5 | 0 | 6 | 3 | 0 | 0 | 0 | 0 | 0 | 0 | 0 |
| Mg | 3 | 0 | 0 | 0 | 0 | 0 | 3 | 0 | 0 | 0 | 3 |

Bicarbonate obtained by metabolism of lactate* or acetate**
***Normosol is a registered trademark of Abbott Laboratories Recuscitation solutions, such as the hypertonic solutions in accordance with this invention, are employed to replace electrolytes and water. Among the isotonic solutions, i.e. those solutions having the same total ionic strength as plasma, the balanced electrolyte solution F of Table I most closely simulates plasma. The solutions A and B both contain excessive chloride Na:Cl ratio of about 1 which after administration distorts the electrolyte balance of normal plasma. The hypertonic solutions contain proportionally more electrolyte than water, hence their use replaces electrolytes with smaller loads of water. The shifts in water and electrolytes after burns, trauma, or hemorrhage result in redistribution of more sodium than water. The loss is hypertonic, thus replacement with a hypertonic solution facilitates replacement without accumulation of excess water. In the injured but not in the normal person or subjects, excess water is retained and results in edema, both local and pulmonary. Additionally, anoxia and acidosis occur after trauma. Replacement with saline (Na:Cl), e.g. solution A, causes accumulation of excess chloride and does not correct the acidosis but actually results in augmenting the acidosis. The hypertonic solutions G and H contain excess bicarbonate and result in elevation in plasma pH and bicarbonate. The overcorrection by the use of such hypertonic solutions is undesirable.

The hypertonic solution in accordance with this invention, solution J of Table I, provides an initial load of bicarbonate, e.g. as its most active precursor acetate, to correct but not overcorrect the acidosis because the Na:Cl ratio is the same as that of plasma. The excess chloride as would be obtained in saline or sodium chloride solutions, e.g. solution A, is avoided by providvival with less volume administered, normal plasma electrolyte values and less edema.

Animal tests were carried out to demonstrate the comparative efficacy of hypo-, iso- and hypertonic sodium solutions in experimental burn shock, all as reported in my above-identified paper. In these tests, female albino mice, weighing 22 to 24 grams, were used. Food and water were given ad libitum up to the beginning of the experiments and withheld for 24 hours subsequently. For burn trauma, unshaven mice were anesthetized with ether and then immersed to the axilla in hot water at a temperature of 72°–73° C. for six or seven seconds. These conditions were selected to obtain 80% mortality rate in 24 hours in untreated mice. Groups of ten mice were kept in metal cages with a bedding of woodchips in a room at 25° C. For metabolic experiments, a slightly less severe scald at 70° C. was used so that urine could be collected without mortality from pooled groups of five treated mice kept in stainless steel metabolism cages.

Fluid therapy was administered intraperitoneally via a No. 26 gauge needle two hours after the burn was inflicted; volumes over 225 ml per kilogram were given in divided doses two and five hours post burn. In each experiment, the scalded animals were divided randomly into groups of 20 to provide one control group and five therapy groups. This schedule limited the number of animals that could be handled in each experiment and hence, each fluid was tested three to five times in different experiments; over 3,000 mice were used.

The sodium concentration of the solutions ranged from 75 to 300 mEq per liter and with various sodium to chloride ratios as indicated in Table II. Hypertonic solutions containing only 100 mEq per liter of chloride and others with sodium to chloride ratios closer to that of plasma were tested. The volume of fluid administered ranged from 37.5 to 346 ml per kilogram of body weight.

TABLE II

COMPOSITIONS OF SOLUTIONS USED (mEq/l)

| Na | Cl | HCO$_3$* | K | Mg | Ca |
|---|---|---|---|---|---|
| 300 | 100 | 200 | 0 | 0 | 0 |
| 300 | 170 | 130 | 0 | 0 | 0 |
| 225 | 100 | 135 | 5 | 2 | 3 |
| 225** | 160 | 75 | 5 | 2 | 3 |
| 225 | 225 | 0 | 0 | 0 | 0 |
| 154 | 154 | 0 | 0 | 0 | 0 |
| 150 | 100 | 58 | 5 | 3 | 0 |
| 140 | 98 | 50 | 5 | 3 | 0 |
| 130 | 126 | 18 | 14 | 5 | 0 |
| 130 | 109 | 28 | 4 | 0 | 3 |
| 100 | 75 | 30 | 4 | 1 | 0 |
| 75 | 56 | 23 | 3 | 1 | 0 |

*HCO$_3$ obtained by metabolism of acetate and d,l-lactate
**Hypertonic solution in accordance with this invention The test results show that maximum survival occurred with sodium intake of 22 to 24 mEq per kilogram of body weight obtained from appropriate volumes of solutions varying from 100 to 300 mEq per liter of sodium. When the sodium intake was reduced, the mortality values were significantly increased as compared with 22.5 mEq per kilogram of sodium. Further reduction in sodium intake to 11.25 or below mEq per kilogram was followed by further increase in mortality rate. The tests showed that the ratio of sodium to chloride was important and in all experiments were the hypertonic solutions contained 160 or 170 mEq per liter of chloride (Na:Cl ratio of about 1.4 like plasma). Higher mortality rates were obtained as compared with hypertonic solutions with a high Na:Cl ratio of about 2:1 or where the solutions contained only Na:Cl, a ratio of 1:1.

The overall results of the tests are summarized in accompanying Table III:

served that with the optimal sodium intake of 22.5 mEq per kilogram, the volume of urine increased as the volume of the administered solution increased. The large volume of urine after the hypotonic fluid would be equivalent to 3 to 4 liters in 24 hours in an adult human and comprise ⅓ of the fluid administered compared to only 1/6 of that administered with hypertonic solutions. As the sodium concentration of the administered fluid was increased, the concentration of sodium in the urine increased also, nevertheless, 85 percent or more of that administered was retained. After the burn at the higher temperature (the more severe injury), the concentration of sodium in the urine was lower than after the less severe burn, suggesting greater retention of sodium with more severe thermal trauma. The percentage of sodium retained exceeded the percentage of water retained. The water excess is most obvious after the hypotonic fluid therapy in which twice as much water is excreted as after other intakes.

The urine potassium and urea concentrations are elevated similarly in proportion to the sodium concentration of the fluid administered and the smaller urine volumes. The excess potassium excretions were approximately 20 percent of the sodium administered; this indicates the portion of administered sodium exchanged with intracellular potassium. The urea nitrogen and potassium excretions, which may be taken as indicative of tissue breakdown and renal function, were approximately similar.

The changes in body weight are compared to the untreated controls, which exhibited negative water balance and lost weight. Among treated animals, the maximum weight loss occurred after the hypertonic fluid; the minimum occurred after isotonic fluid therapy, with maximal retention of Na and Cl.

Previous investigators found that maximal survival after extensive thermal trauma was attained by administration of 15 to 18 percent of body weight of an isotonic sodium salt solution. This delivers 22.5 to 24 mEq per kilogram of sodium, the optimum intake found in

TABLE III

COMPARATIVE EFFICACY OF VARIOUS SODIUM SOLUTIONS IN TERMS OF VOLUME OF FLUID ADMINISTERED

| Sodium Solution (mEq/L) | | Amount of Fluid Administered (ml)/Kg Body Weight | | | | | | | | |
|---|---|---|---|---|---|---|---|---|---|---|
| | | 300 | | 200 | | 150 | | 100 | | 50 | |
| Na | Cl | Mortality (%)* | Na** (mEq) | Mortality (%)* | Na** (mEq) | Mortality (%)* | Na** (mEq) | Mortality (%)* | Na** (mEq) | Mortality (%)* | Na** (mEq) |
| 300 | 170 | — | — | — | — | 20 | 45 | 0 | 30 | 8*** | 15 |
| 225 | 160 | — | — | — | — | 10 | 34 | (3) | (23) | 8*** | 11 |
| 150 | 100 | 5 | 45 | 0 | 30 | (9) | (23) | 6 | 15 | 27 | 8 |
| 130 | 109 | 5 | 39 | (8) | (26) | 5 | 20 | 13 | 13 | 10 | 7 |
| 100 | 75 | 22 | 30 | (10) | (20) | 14 | 15 | 33 | 10 | 35 | 5 |
| 75 | 56 | (19) | (23) | 20 | 15 | — | — | 20 | 30 | 4 | |

*Percent of treated mice that died in 24 hrs: 78% of 310 untreated mice died in 24 hrs.
**Intake of sodium in millequivalents per kilogram of body weight.
***These solutions in this dosage were more effective (P < 0.005).
( )Solution intake values in parenthesis demonstrate those which delivered optimum sodium intake.

The overall test results suggest that excess sodium with too little water or excess water with too little sodium are deleterious with the lowest fluid intake (50 ml per kilogram) the hypertonic solutions were significantly more effective. The hypertonic solutions were effective in minimal volume whereas the other solutions, the non-hypertonic solutions, required substantially larger volumes.

With respect to changes in electrolytes, urine volumes and body weight after fluid therapy, it was obtests herein with solutions ranging from 100 to 300 mEq per liter of sodium.

After thermal injury, the therapeutic goal is to restore circulatory, pulmonary and renal function. The influx of sodium into the burned regions, which exceeds their gain in water, reduces the total "available" sodium. In man, experimental sodium loss resulted in severe circulatory and renal dysfunction. In animals similar events occur, together with a marked fall in O$_2$ consumption, glucose utilization, cardiac output and respiratory control efficency after sodium removal produced with minimal changes in body water and potassium. Severe burns are further complicated by metabolic acidosis which depresses renal function and is responsive to alkali therapy. Because of these dangerous physiological consequences "lost" sodium needs to be replaced with appropriate anions.

The tests carried out demonstrate that the administration of solutions other than hypertonic solutions result in substantial weight gain and edema, however, resuscitation with hypertonic alkaline solutions in accordance with this invention is accomplished with less fluid intake, less gain in weight, less edema and with urine output averaging 30 ml per hour. With hypertonic solutions the required sodium intake is achieved with relatively low volume of 75 to 100 ml per kilogram and less weight gain occurred whereas with the administration of isotonic solutions the volume increased to the range from 150 to 300 ml per kilogram. The hypotonic solutions required the largest fluid intake of 225 to 300 ml per kilogram and the 75 mEq per liter solution resulted in considerably higher mortality rate.

The hypertonic solutions in accordance with this invention, particularly the solution containing per liter 225 mEq sodium and 160 mEq chloride clearly offers the advantages of resuscitation with less fluid intake and early onset of adequate urine and sodium excretion. The results reported hereinabove in connection with the solutions set forth in Table II and the data being summarized in Table III and other pertinent data as indicated hereinabove are set forth in my above-referred paper "Comparative Efficacy of Hypo-, Iso- and Hypertonic Sodium Solutions in Experimental Burn Shock", which appeared in SURGERY, Vol. 75, No. 1, pp. 71–79, January 1974.

As will be apparent to those skilled in the art in the light of the foregoing disclosure, many modifications, alterations and substitutions are possible in the practice of this invention without departing from the spirit or scope thereof.

I claim:

1. An aqueous hypertonic solution suitable for administration to humans for the treatment of trauma comprising on the basis of 1 liter of solution about 200–300 mEq sodium, about 145–215 mEq chloride, about 55–85 mEq bicarbonate or acetate or lactate, the sodium to chloride ratio being about 1.4.

2. A solution in accordance with claim 1 having a pH of about 8–8.3.

3. A solution in accordance with claim 1 wherein the pH of the solution is adjusted to a value of about 6.0 by the addition of hydrochloric acid.

4. A solution in accordance with claim 1 containing about 1.5–2.5 mEq magnesium.

5. A solution in accordance with claim 1 containing about 3.5–5.5 mEq potassium.

6. A solution in accordance with claim 1 containing about 3–5.5 mEq calcium.

7. A solution in accordance with claim 1 containing about 2.5–3.5 mEq phosphates.

8. A solution in accordance with claim 1 wherein the solution has a sodium to chloride ratio about the same as that of normal human plasma.

9. An aqueous hypertonic solution suitable for administration to humans for the treatment of trauma comprising on the basis of 1 liter of solution about 200–300 mEq sodium, about 145–215 mEq chloride, about 55–85 mEq bicarbonate or acetate or lactate, about 1.5–2.5 mEq magnesium, about 3.5–5.5 mEq potassium, and about 3–5.5 mEq calcium, the sodium to chloride ratio being about 1.4.

10. A solution in accordance with claim 9 having a pH of about 8.3.

11. A solution in accordance with claim 9 wherein the pH is adjusted to about 6.0.

12. A solution in accordance with claim 9 containing about 225 mEq sodium, about 160 mEq chloride, about 73 mEq lactate, about 5 mEq potassium and about 1.5–2.5 mEq magnesium.

13. A solution in accordance with claim 9 containing about 235 mEq sodium, about 160 mEq chloride, about 75 mEq lactate, about 2 mEq magnesium, about 5 mEq potassium, about 3 mEq calcium, the pH of the solution being adjusted to about 6.0 by the addition of hydrochloric acid.

14. A solution in accordance with claim 9 containing about 235 mEq sodium, about 160 mEq chloride, about 75 mEq acetate, about 2 mEq magnesium, about 5 mEq potassium, about 3 mEq calcium, the pH of the solution being adjusted to about 8.3 by the addition of hydrochloric acid.

* * * * *

UNITED STATES PATENT AND TRADEMARK OFFICE
CERTIFICATE OF CORRECTION

PATENT NO. : 3,993,750
DATED : November 23, 1976
INVENTOR(S) : Charles L. Fox, Jr.

It is certified that error appears in the above–identified patent and that said Letters Patent are hereby corrected as shown below:

Column 1, line 15, "sections" should correctly read
-- solutions --

Column 5, line 33, "were" should correctly read -- where --

Column 5, line 62 should correctly read -- dium are deleterious. With the lowest fluid intake (50 ml --

Columns 5 and 6, under Table III, 10th column, last line, "30" should read -- 8 --
11th column last line, "4" should read -- 30 --; and 12th column, last line should read -- 4 --

Column 7, line 1, "efficency" should correctly read -- efficiency --

Signed and Sealed this

First Day of March 1977

[SEAL]

Attest:

RUTH C. MASON
Attesting Officer

C. MARSHALL DANN
Commissioner of Patents and Trademarks